United States Patent [19]

Rovel et al.

[11] Patent Number: 4,482,458
[45] Date of Patent: Nov. 13, 1984

[54] PROCESS AND APPARATUS FOR THE ANAEROBIC TREATMENT OF WASTE WATER IN A FILTER INCLUDING GRANULAR MATERIAL

[75] Inventors: Jean-Marie Rovel, Rueil-Malmaison; Claude Prévot, Ville D'Avray; Roger Nicol, Vanves, all of France

[73] Assignee: Degremont, Hauts de Seine, France

[21] Appl. No.: 534,621

[22] Filed: Sep. 22, 1983

[30] Foreign Application Priority Data

Sep. 28, 1982 [FR] France ................. 82 16273

[51] Int. Cl.³ .............. C02F 3/28; C12M 1/08
[52] U.S. Cl. .................... 210/603; 210/617; 210/150; 48/111; 48/197 A; 435/167; 435/314
[58] Field of Search ............... 210/150, 603, 615, 616, 210/617, 618, 151, 188, 218; 422/140, 142, 147; 435/167, 313, 314; 48/197 A, 111

[56] References Cited

U.S. PATENT DOCUMENTS

| | | | |
|---|---|---|---|
| 2,889,929 | 6/1959 | Kivell | 210/603 |
| 3,788,476 | 1/1974 | Othmer | 210/194 |
| 3,853,752 | 12/1974 | Tymoszczuk | 210/150 |
| 3,968,034 | 7/1976 | Tymoszczuk | 210/151 |
| 4,009,099 | 2/1977 | Jeris | 210/618 |
| 4,111,808 | 9/1978 | Fair | 210/209 |
| 4,198,211 | 4/1980 | Shattock | 210/603 |
| 4,256,573 | 3/1981 | Shimodaira et al. | 210/618 |
| 4,322,296 | 3/1982 | Fan et al. | 210/618 |

FOREIGN PATENT DOCUMENTS

| | | |
|---|---|---|
| 0026163 | 7/1980 | European Pat. Off. . |
| 2189328 | 6/1973 | France . |
| 2446259 | 1/1979 | France . |
| 148112 | 6/1976 | Netherlands . |
| 1527766 | 11/1975 | United Kingdom . |

*Primary Examiner*—Benoit Castel
*Attorney, Agent, or Firm*—Wenderoth, Lind & Ponack

[57] ABSTRACT

Waste water to be treated is introduced into a filter including granular material for supporting the biomass resulting from an anaerobic treatment operation. During such treatment operation biogas is formed, and the waste water being treated and the granular material supporting the biomass are continuously circulated by injecting a portion of the biogas into a tube extending vertically upwardly through the filter.

8 Claims, 1 Drawing Figure

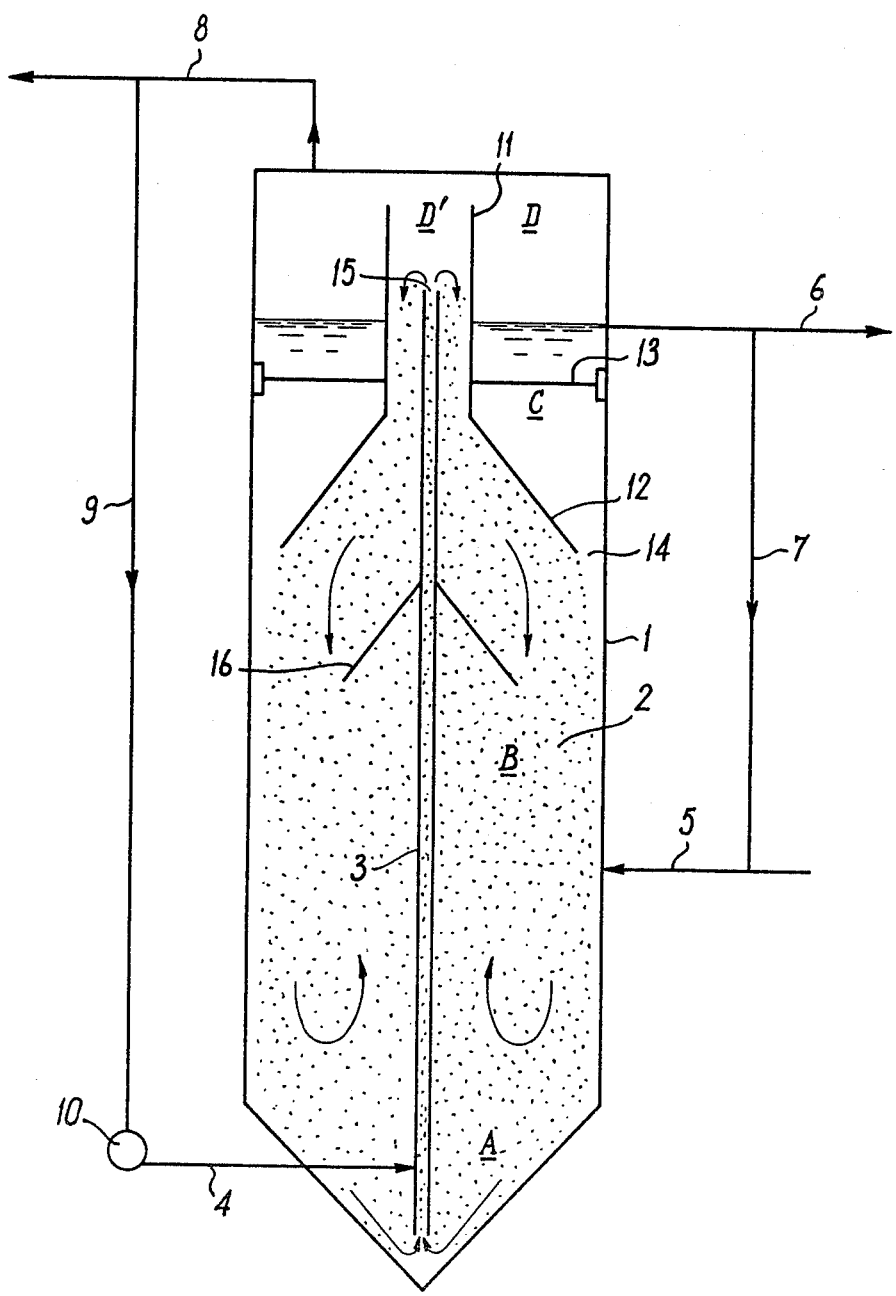

PROCESS AND APPARATUS FOR THE ANAEROBIC TREATMENT OF WASTE WATER IN A FILTER INCLUDING GRANULAR MATERIAL

BACKGROUND OF THE INVENTION

The present invention relates to a process and apparatus for the anaerobic treatment of municipal or industrial waste water with the simultaneous production of biogas, e.g. methane, carbon dioxide, etc. More particularly, the present invention relates to such a treatment process and apparatus by which the waste water is subjected to the action of anaerobic micro-organisms in a filter containing a granular filler material to which the resultant biomass attaches itself. A number of systems of this general type are known, in which known systems the waste water to be treated is passed from bottom to top or from top to bottom of an anaerobic filter material which is to be filled with a stationary or movable supporting material. Several types of systems are known in which the supporting material is stationary. The material can be immersed and passed from top to bottom by the water which is to be treated. The treatment time therefore is very short and requires a high return rate. The supporting material can be immersed, with the water to be treated circulating from top to bottom or from bottom to top. If an orderly supporting material is used, e.g. a plastic material, such material has a small specific surface, so that only a small quantity of biomass can attach itself thereto. Also, problems arise concerning the distribution of the water to be treated and the recirculated water. If a loosely packed or granular material is used (e.g. clay, flint), there is a serious risk of clogging the filter, the biomass having a tendency to grow and to block the free flow of water, and the water flow rate being too low to tear away the excess biomass.

Systems also are known in which the supporting material is, for example, movable, expanded or fluidized by the water to be treated and by the recirculated water. However, in this type of system there is the risk of clogging the devices which feed such fluids, and there are serious problems regarding the spreading of the water to be treated and of the circulated water. In addition, some of these known systems require settling of the treated water outside the filter itself.

SUMMARY OF THE INVENTION

With the above discussion in mind, the object of the present invention is to provide an improved process and apparatus for the anaerobic treatment of waste water, whereby it is possible to overcome the prior art disadvantages, and furthermore whereby it is possible to allow a simple and easy adjustment of the treatment operation.

This object is achieved in accordance with the present invention by the provision of a process and apparatus for the anaerobic treatment of waste water, during which treatment there is formed biogas. There is provided a filter including granular material for supporting the biomass resulting from the anaerobic treatment. The waste water to be treated is introduced into such filter. The waste water being treated and the granular material supporting the biomass are continuously circulated by means of a pumping system utilizing as a driving fluid a portion of the biogas produced during the treatment. The pumping system employed in accordance with the present invention includes at least one tube extending vertically through the filter, into which tube is injected the portion of the biogas produced during the anaerobic treatment. The injection of the gas into the tube creates a pumping action upwardly through the tube, and this pumping action achieves a continuous circulation of the water being treated and the granular material. The concept of this type of vertical tube, or a plurality of such vertical tubes, into which is/are introduced a pressurized gas is disclosed in U.S. Pat. No. 4,111,808, the disclosure of which is incorporated herein by reference. This patent discloses a system for the treatment of primary sludge by the use of such a pumping system. The present invention however involves the anaerobic treatment of waste water by means of a filter including a granular material supporting the biomass resulting from the anaerobic treatment, while employing such a pumping system to achieve continuous circulation of the water being treated and the granular material supporting the biomass. In accordance with the present invention, the biogas which is formed simultaneously during the treatment of the waste water is used as the driving fluid of the pumping system. Preferably, the biogas is compressed to a high overpressure prior to injection into the tube or tubes. The rate of circulation of the granular material and the water being treated is regulated by controlling the flow of the biogas into the pumping system. Thus, the flow rate of the biogas is regulated as a function of the desired rate or velocity of circulation of the granular material and water being treated. In fact, the quantity of material caused to circulate or whirl is a function of the variation in density of the granular material between the beginning phase when the seeding of the granular material by the anaerobic micro-organisms is not yet effective and its equilibrium condition when the granular material is coated with the biomass. The simple and accurate control of the flow of the biogas results in a constant turbulence as well as in an optimum quantity of circulating material per unit of volume of the filter.

In accordance with a specific feature of the present invention, the filter is provided in an enclosure which defines four successively superposed zones. A lower zone is for compacting and delivering the water being treated and the granular material supporting the biomass into a lower portion of the tube. Above the lower zone is a turbulence zone through which are continuously circulated the water being treated and the granular material supporting the biomass. Above the turbulence zone is a decanting zone from which treated water is withdrawn. Above the decanting zone is a collecting zone for collecting the biogas formed during the treatment. Granular material supporting the biomass which enters the decanting zone falls back under the force of gravity into the turbulence zone, with the settled treated water being drained off from a settling zone. A portion of the treated water may be recirculated with waste water to be treated into the turbulence zone.

The granular material employed (e.g. pumice stone, expanded clay, activated coal, plastic material) is made up of particles which preferably are smaller than 1 mm in diameter, which have a good specific surface, and which have good resistance to abrasion. The density of the granular material is such that the difference between the densities of the granular material coated with the biomass and of the water being treated is less than 0.3, and preferably is between 0.05 and 0.15.

The process, like all anaerobic treatment processes, is best carried out at a temperature of 35° C.

BRIEF DESCRIPTION OF THE DRAWING

The above and other objects, features and advantages of the present invention will be apparent from the following detailed description, with reference to the accompanying drawing, wherein the singe FIGURE is a schematic view of an apparatus according to the present invention and illustrating the process of the present invention.

DETAILED DESCRIPTION OF THE INVENTION

The drawing and the following description are of one embodiment of the present invention. It is to be understood that this is exemplary only and is not intended to be limiting of the scope of the present invention. Specifically, attention is directed to the fact that the illustrated pumping system includes a single vertical tube. However, it is to be understood that the present invention encompasses the use of plural such tubes.

Shown in the drawing is an enclosure 1 containing a filter including granular material 2. Waste water to be treated is introduced into the filter by a conduit 5. Anaerobic treatment of the waste water by anaerobic micro-organisms occurs in a manner known to those skilled in the art, with a biomass resulting, and such biomass becomes attached to and is supported by the granular material 2. A biogas, e.g. methane, simultaneously is produced and works its way upwardly through the granular material 2 and is withdrawn from the top of the enclosure by a conduit 8. Treated water is settled or decanted and is withdrawn at a conduit 6, and a portion of the treated water may be recirculated to the waste water conduit 5 by means of a conduit 7.

In accordance with the present invention there is provided a pumping system for continuously circulating the waste water being treated and the granular material 2 supporting the biomass. This pumping system includes a vertical tube 3 extending vertically through the filter within the enclosure 1. At least a portion of the biogas from conduit 8 is passed by a conduit 9, a booster or pressure pump 10 and a conduit 4 and is injected into tube 3. The injection of the biogas into the tube 3 creates a pumping action upwardly through the tube, and this pumping action achieves a continuous circulation of the granular material 2 supporting the biomass and the water being treated. This continuous circulation generally is indicated by the arrows in the drawing.

The interior of the enclosure defines therein four successively superposed zones. A lower zone A achieves compacting or concentrating of the recirculating material and delivery thereof into the lower portion of the tube 3. This action is facilitated by the configuration of the bottom of the enclosure, such as the conical shape shown in the drawing. A turbulence zone B is above lower zone A. In zone B the water being treated and the granular material supporting the biomass circulate continuously. It is in this zone that the anaerobic treatment substantially occurs. The degree of turbulence of the granular material supporting the biomass and the water being treated, and thereby the extent of intimate contact between the biomass, the granular material and the water being treated, is increased in zone B by the provision of at least one deflector 16 connected to tube 3. Those skilled in the art will be able to understand how to regulate this degree of turbulence by the number of and configuration of deflectors 16. Above the turbulence zone is a decanting or settling zone C. This zone substantially is defined by a funnel 11 surrounding the upper part of tube 3 and having a base in the form of a downwardly and outwardly flared wall 12 substantially covering the upper portion of turbulence zone B. An adjustable fastening arrangement 3 enables variation of the position of the funnel in the interior of the enclosure 1, and this adjustment of position would be made depending on the quality of water being treated. The treated water is removed from zone C by conduit 6, while granular material supporting the biomass which enters zone C falls downwardly under the force of gravity into the turbulence zone B through a space 14 between the wall 12 of the funnel and the inner wall of enclosure 1 i.e., the granular material has a greater density than the water being treated. Above zone C is a collecting or storage zone D for storing the biogas produced during the anaerobic treatment. Substantial degasification of the water occurs at the outlet 15 of the tube 3 in a zone D' defined by the upper part of funnel 11. The biogas collected in zone D' then is withdrawn by conduit 8.

Pump 10 pressurizes the portion of the biogas before injection thereof into the tube 3. The rate of flow of the biogas injected into the tube is regulated as a function of the desired velocity of circulation. In other words, the rate of circulation of the granular material supporting the biomass and the water being treated is regulated by controlling the flow of biogas introduced into tube 3. This rate of circulation will be a function of the difference in densities between the granular material supporting the biomass and the water being treated. Such density difference is less than 0.3 and preferably is from 0.05 to 0.15. Those skilled in the art will understand how to achieve a desired circulation with the resultant equilibrium treatment by means of regulation of the flow of the injected biogas, for a given installation. Those skilled in the art also will understand what granular materials should be employed to achieve densities of the granular material supporting the biomass and the water being treated to achieve desired regulation of the circulation rate.

The following is one example of a treatment installation in accordance with the present invention. It is to be understood however that this is an example only and is not limiting to the scope of the present invention. An enclosure with an overall height of 5 meters included a zone A of 0.5 meters, a zone B of 3 meters, and a zone C of 1 meter. The surface area of the enclosure was $2^2$ meters. The bottom of the enclosure was conical and had an angle of inclination of 45°. Waste water injected through conduit 5 was an essentially soluble and biodegradable pollution and had an average COD of 4 g/l. Such waste water was introduced at a rate of 1.5 m$^3$/h. The flow of biogas injected into tube 3 initially was 6 m$^3$/h, and after equilibrium was reached was adjusted to 4 m$^3$/h. After achieving equilibrium, from 2.5 to 3.0 Nm$^3$/h of biogas containing 60 to 70% methane was produced. The treated water removed by conduit 6 had a COD of 600 mg/l and 300 mg/l materials in suspension.

Although the present invention has been described and illustrated with respect to a preferred embodiment, various modifications and changes may be made without departing from the scope of the present invention. Furthermore, it is to be understood that the concept of the present invention involves certain features known in the art, for example the general technology of anaerobic treatment of waste water.

We claim:

1. A process for the anaerobic treatment of waste water, during which treatment there is formed biogas, said process comprising:

providing an enclosure having therein a filter including granular material having a density greater than that of the waste water to be treated;

introducing waste water to be treated into said enclosure, whereby said water circulates upwardly through said filter during an anaerobic treatment resulting in formation of biomass which is supported by said granular material and resulting in formation of said biogas;

collecting said biogas at an upper portion of said enclosure above said filter and said waste water to be treated;

providing at least one tube extending vertically upwardly through said filter;

withdrawing said collected biogas and compressing at least a portion thereof;

injecting into said tube said compressed biogas, thereby creating a pumping action upwardly through said tube, and thereby continuously circulating said waste water being treated and said granular material supporting said biomass upwardly through said tube and downwardly through a turbulence zone exteriorly of said tube, said anaerobic treatment substantially occurring in said turbulence zone;

decanting and removing treated water from said enclosure at a position above said turbulence zone; and regulating the rate of said circulation of said granular material and said waste water by controlling the flow of said compressed biogas as a function of the difference in densities between said granular material supporting said biomass and said water being treated.

2. A process as claimed in claim 1, comprising providing said density difference to be less than 0.3.

3. A process as claimed in claim 1, comprising providing said density difference to be from 0.05 to 0.15.

4. A process as claimed in claim 1, comprising providing the particles of said granular material of a size having a diameter of less than 1 mm.

5. An apparatus for the anaerobic treatment of waste water, during which treatment there is formed biogas, said apparatus comprising:

an enclosure having therein a filter including granular material having a density greater than that of the waste water to be treated;

means for introducing waste water to be treated into said enclosure, whereby said waste water circulates upwardly through said filter during an anaerobic treatment resulting in formation of biomass which is supported by said granular material and resulting in formation of said biogas;

said enclosure defining therein four successively superposed zones including a lower zone, a turbulence zone above said lower zone, a decanting zone above said turbulence zone, and a collecting zone above said decanting zone and wherein said biogas is collected;

at least one tube extending vertically upwardly through said filter;

a funnel surrounding an upper portion of said tube and partially defining said decanting zone, said funnel having an outwardly and downwardly flared base portion extending over an upper portion of said turbulence zone;

means for withdrawing said biogas from said collecting zone and for passing at least a portion of said biogas to said tube;

means for compressing said portion of said biogas;

means for injecting said compressed biogas into said tube, thereby creating a pumping action upwardly through said tube, and thereby continuously circulating said waste water being treated and said granular material supporting said biomass upwardly through said tube and downwardly through said turbulence zone exteriorly of said tube, said anaerobic treatment substantially occurring in said turbulence zone; and means for removing treated water from said decanting zone.

6. An apparatus as claimed in claim 5, wherein said introducing means introduces said water to be treated into said granular material in said turbulence zone.

7. An apparatus as claimed in claim 5, further comprising at least one deflector means connected to said tube within said turbulence zone for promoting therein turbulence of the water being treated and said granular material.

8. An apparatus as claimed in claim 5, wherein the particles of said granular material have a diameter of less than 1 mm.

* * * * *